(12) United States Patent
Fukui et al.

(10) Patent No.: US 8,012,755 B2
(45) Date of Patent: Sep. 6, 2011

(54) WATER QUALITY EVALUATION METHOD AND SUBSTRATE CONTACTING APPARATUS USED

(75) Inventors: Takeo Fukui, Tokyo (JP); Ikunori Yokoi, Tokyo (JP); Tetsuo Mizuniwa, Tokyo (JP)

(73) Assignee: Kurita Water Industries Ltd., Tokyo (JP)

(*) Notice: Subject to any disclaimer, the term of this patent is extended or adjusted under 35 U.S.C. 154(b) by 819 days.

(21) Appl. No.: 11/840,726

(22) Filed: Aug. 17, 2007

(65) Prior Publication Data

US 2008/0044924 A1 Feb. 21, 2008

(30) Foreign Application Priority Data

Aug. 21, 2006 (JP) ................................. 2006-224401

(51) Int. Cl.
*G01N 33/18* (2006.01)
*G01N 33/20* (2006.01)

(52) U.S. Cl. ......... 436/5; 73/61.41; 73/61.42; 73/61.59; 73/61.62; 73/61.71; 73/61.72; 73/64.56; 73/864.71; 356/36; 356/38; 436/73; 436/171; 436/172; 436/173; 436/174; 436/178; 436/181; 436/182

(58) Field of Classification Search .................. 73/53.01, 73/61.41–61.42, 61.59, 61.62, 61.71–61.72, 73/64.56, 863.21, 864.71; 134/21, 26; 356/36, 356/38; 422/99, 102–104; 436/4–5, 73, 436/79–84, 139–142, 155, 171–174, 178, 436/181–182
See application file for complete search history.

(56) References Cited

U.S. PATENT DOCUMENTS

| | | | | |
|---|---|---|---|---|
| 3,926,306 A | * | 12/1975 | Van Nederveen | 206/524.8 |
| 4,886,162 A | * | 12/1989 | Ambrogio | 206/710 |
| 4,969,556 A | * | 11/1990 | Ishimaru et al. | 206/524.8 |
| 4,990,459 A | * | 2/1991 | Maeda et al. | 436/178 |
| 5,137,063 A | * | 8/1992 | Foster et al. | 141/98 |
| 5,162,233 A | * | 11/1992 | Komori et al. | 436/155 |
| 5,255,783 A | * | 10/1993 | Goodman et al. | 206/711 |
| 5,284,802 A | * | 2/1994 | Muraoka et al. | 438/708 |
| 5,422,925 A | * | 6/1995 | Komatsu et al. | 378/45 |
| 5,426,057 A | * | 6/1995 | Tamaoki | 436/146 |
| 5,474,177 A | * | 12/1995 | Abrams et al. | 206/710 |
| 5,476,006 A | * | 12/1995 | Fujii et al. | 73/105 |
| 5,549,205 A | * | 8/1996 | Doche | 206/710 |
| 5,569,837 A | * | 10/1996 | Hinaga | 73/19.01 |
| 5,686,314 A | * | 11/1997 | Miyazaki | 436/177 |
| 5,849,103 A | * | 12/1998 | Bennett et al. | 134/22.18 |
| 5,994,142 A | * | 11/1999 | Yamasaki et al. | 436/73 |
| 6,037,182 A | * | 3/2000 | Weems | 436/75 |
| 6,228,651 B1 | * | 5/2001 | Fukuda et al. | 436/57 |
| 6,320,655 B1 | * | 11/2001 | Matsushita et al. | 356/237.2 |
| 6,422,823 B2 | * | 7/2002 | Bernard et al. | 417/18 |
| 6,637,998 B2 | * | 10/2003 | Langan et al. | 414/217 |
| 6,897,070 B2 | * | 5/2005 | Blalock | 436/73 |

FOREIGN PATENT DOCUMENTS

JP 2000-321266 * 11/2000

(Continued)

*Primary Examiner* — Arlen Soderquist
(74) *Attorney, Agent, or Firm* — J.C. Patents (57) ABSTRACT

A water quality evaluation method capable of evaluating quality of water to be evaluated with high precision and a substrate contacting apparatus used in the water quality evaluation method are provided. The substrate contacting apparatus 10 has a sealing performance keeping the interior at a vacuum degree lower than or equal to −0.094 MPa. A substrate W is accommodated in the substrate contacting apparatus 10 and water to be evaluated is fed therein, after stopping feeding water, the interior of the substrate contacting apparatus 10 is sealed, and the substrate contacting apparatus 10 is sent to an analysis device with the substrate W accommodated therein.

6 Claims, 7 Drawing Sheets

FOREIGN PATENT DOCUMENTS

| | | | |
|---|---|---|---|
| JP | 2001-208748 | | 8/2001 |
| JP | 2001-228138 | * | 8/2001 |
| JP | 2001-237289 | * | 8/2001 |
| JP | 2003-254908 | * | 9/2003 |
| JP | 2005-274400 | | 10/2005 |
| JP | 2007-256181 | * | 10/2007 |

* cited by examiner

WATER QUALITY EVALUATION METHOD AND SUBSTRATE CONTACTING APPARATUS USED

CROSS-REFERENCE TO RELATED APPLICATION

This application claims the priority benefit of Japan application serial no. 2006-224401, filed Aug. 21, 2006. All disclosure of the Japan application is incorporated herein by reference.

BACKGROUND OF THE INVENTION

1. Field of the Invention

The present invention relates to a water quality evaluation method of ultrapure water applicable in the industry of electronic materials such as semiconductor and liquid crystal. More particularly, the present invention relates to a preferred evaluation method in the condition that the water quality of ultrapure water is evaluated by contacting the ultrapure water and a substrate, such as a semiconductor wafer, to perform surface analysis on the substrate. The present invention further relates to a substrate contacting apparatus used by the water quality evaluation method.

2. Description of Related Art

Ultrapure water used in the field of electronic industry is the last substance contacting wafers in a cleaning step, so the concentrations of impurities contained in the ultrapure water will have influence on the cleanliness of the surfaces of substrates represented by silicon. Therefore, in the semiconductor field, with the increase of integration, the concentration of impurities in the ultrapure water used during the manufacturing must be reduced. In recent years, researchers have endeavored to reduce all the impurities contained in the ultrapure water. Accordingly, a technique of analyzing ultra-trace impurities in the water by using an analysis device with high sensitivity has been developed.

However, in recent years, with the sharp improvement of the performance of semiconductor products, even ultrapure water, in which ultra-trace impurities have been definitely analyzed, is used to perform cleaning step, the quality standard of the product still cannot be satisfied.

The organics that are likely to affect the quality of the semiconductor products are various and cannot be determined, and the amount of the impurities in the ultrapure water is of ng/L scale and being ultra micro and is lower than or equal to the lower limit of analysis, so it is difficult to control the water quality. Additionally, even in a circumstance that a substance exists in the ultrapure water in an extreme micro amount, if the material is easily to be attached on the substrate due to co-existing substances, it will have undesired influence on the substrate, which is difficult to be controlled even the ultrapure water quality is analyzed directly, so the water quality evaluation cannot be properly performed.

In order to solve this problem, a water quality evaluation method is developed in the industry, which includes contacting a substrate such as a semiconductor wafer with water to be evaluated such that the impurities in the water to be evaluated attach on the substrate; analyzing the attachments on the substrate surface, or eluting the attachments and analyzing the eluant, or analyzing the changes on the substrate surface, so as to evaluate the water quality.

For example, a method of detecting metals attached on a substrate surface by using total reflection fluorescence X-ray analysis is disclosed in JP Patent Publication No. 2001-208748. Additionally, a method of detecting organics attached on a substrate surface by using Fourier transform infrared spectrometry (FTIR) or thermal desorption gas chromatograph mass spectrometer (TDGCMS) is disclosed in JP Patent Publication No. 2005-274400.

According to the above water quality evaluation methods, the influence of the water to be evaluated on the substrate is actually known, and thus the impurities in the water to be evaluated which have influence on the substrate can be determined.

Moreover, according to JP Patent Publications No. 2001-208748 and No. 2005-274400, the substrate is accommodated in a retention container (substrate contacting apparatus), and water to be evaluated is fed into the retention container to contact the substrate, and then the substrate is taken out of the retention container and placed in a sealed container and transported to an analysis device to be analyzed.

[Reference 1] JP Patent Publication No. 2001-208748.
[Reference 2] JP Patent Publication No. 2005-274400.

According to the evaluation method of JP Patent Publication No. 2001-208748 and No. 2005-274400, in order to prevent impurities in the air from attaching on the substrate surface when taking the substrate out of the retention container, a step of feeding water to the retention container must be performed in a place having clean gas environment, such as a clean room, or near such a place.

Preferably, except to opening the retention container to accommodate the substrate in the container or take the substrate out of the container in a clean room, in any steps, the retention container accommodating the substrate must be completely sealed.

That is to say, after accommodating the substrate in the retention container in a clean room, or when transporting the retention container to a position where the water to be evaluated contacts with the substrate (the water to be evaluated will be fed into the retention container), or when feeding the water to be evaluated into the retention container, and when transporting the retention container with the substrate accommodated therein to an analysis device after stopping feeding water, it is desired to keep the substrate in the retention container isolated from the air (external gas).

Particularly, when equipment with high precision is required to perform the substrate surface analysis and the place of the analysis device is limited, it takes some time to transport the retention container to the analysis device after contacting the water to be evaluated and the substrate, and the available time of the analysis device is limited, so the substrate must be kept in the retention container for a long time. Therefore, it is desired to keep the retention container to be sealed for a long time.

Furthermore, if the interior of the retention container cannot be keep at an enough vacuum degree, a little amount of air still contacts the substrate in the retention container, thus causing changes on the substrate surface state due to the contaminations and oxygen gas in the air. As a result, it is difficult to determine whether the changes on the substrate surface state are caused by the water to be evaluated or the contact with the air. Moreover, if the substrate surface state changes due to the contact with the water to be evaluated and further changes due to the contact with the air, it is difficult to evaluate water quality with high precision (to determine the amount of metals or organics in the water to be evaluated).

For example, if alkali substances, such as ammonia and amine, exist in the water to be evaluated, depressions and protrusions will be formed on the substrate surface due to etching effect. However, when the air contacts the substrate surface, the contaminations in the air are attached on the substrate surface, or an oxide film is formed on the substrate surface due to the oxygen gas in the air, the height of the depressions and protrusions is reduced.

SUMMARY OF THE INVENTION

Accordingly, the present invention is directed to providing a water quality evaluation method capable of evaluating the water quality of the water to be evaluated with high precision, and a substrate contacting apparatus used by the water quality evaluation method.

The substrate contacting apparatus for evaluating water quality of the present invention is used to accommodate a substrate therein such that the substrate contacts the water to be evaluated, which is characterized in that the interior is kept at a vacuum degree lower than or equal to $-0.094$ MPa.

The water quality evaluation method of the present invention is characterized in that the substrate is accommodated in the substrate contacting apparatus of the present invention, water to be evaluated is fed into the substrate contacting apparatus to contact the substrate, after stopping feeding the water to be evaluated, the interior of the substrate contacting apparatus is sealed and the substrate contacting apparatus is transported to an analysis device, and then the substrate is taken out of the substrate contacting apparatus, and the substrate surface state is determined to evaluate the water quality of the water to be evaluated.

In the water quality evaluation method according to the present invention, the determining of the substrate surface state is determining the depressions and protrusions of the substrate surface.

In the water quality evaluation method according to the present invention, the depressions and protrusions of the substrate surface is determined by a scanning probe microscope.

In the water quality evaluation method according to the present invention, the scanning probe microscope is an atomic force microscope (AFM).

In the water quality evaluation method according to the present invention, the determining of the substrate surface state is determining substances attached or formed on the substrate surface.

In the water quality evaluation method according to the present invention, the substances attached or formed on the substrate surface are determined by fluorescence X-ray analysis, gas chromatograph-mass spectrometry, or Auger electron spectroscopy analysis.

EFFECTS OF THE INVENTION

The substrate contacting apparatus for evaluating water quality of the present invention has high sealing performance that can keep the interior at a vacuum degree lower than or equal to $-0.094$ MPa. Therefore, the invasion of the air (external gas) into the substrate contacting apparatus to contact the substrate can be completely prevented.

Furthermore, in the present invention, the so-called vacuum degree refers to pressure difference between the atmospheric pressure and the pressure in the substrate contacting apparatus (expressed in gauge pressure). That is to say, when the pressure in the substrate contacting apparatus is equal to the atmospheric pressure, the vacuum degree is 0 MPa; when the interior of the substrate contacting apparatus is in a complete vacuum state, the vacuum degree is $-0.1013$ MPa. Accordingly, the vacuum degree is expressed by a value in the range of 0 to $-0.1013$ MPa.

However, when determining the vacuum degree, it is possible to cause difference due to the used vacuum pump, so in the present invention, a vacuum pump having an ultimate vacuum degree of $-0.1012$ MPa, a pumping speed of 20 NL/min is used to vacuum the interior of the substrate contacting apparatus.

In the water quality evaluation method according to the present invention, the substrate is accommodated in the substrate contacting apparatus of the present invention, the water to be evaluated is fed into the substrate contacting apparatus to contact the substrate, then stop feeding the water to be evaluated, the interior of the substrate contacting apparatus is sealed, and the substrate contacting apparatus is transported to an analysis device, afterwards, the substrate is taken out of the substrate contacting apparatus, the substrate surface state is determined to evaluate the quality of the water to be evaluated. As the substrate contacting apparatus has high sealing performance as described above, after the water to be evaluated contacts the substrate, the air is prevented or significantly inhibited from invading into the substrate contacting apparatus to contact the substrate. Therefore, the substrate is completely or almost not influenced by the air, such that the evaluation of the quality of the water to be evaluated (determining amounts of metals or organics in the water to be evaluated) can be performed with high precision.

In the present invention, preferably, the determining of the substrate surface state is determining the depressions and protrusions of the substrate surface.

The depressions and protrusions of the substrate surface can be determined by a scanning probe microscope in detail. The scanning probe microscope is preferably an AFM.

Additionally, in the present invention, the determining of the substrate surface state is determining substances attached or formed on the substrate surface.

The substances attached or formed on the substrate surface are determined by fluorescence X-ray analysis, gas chromatograph-mass spectrometry, or Auger electron spectroscopy analysis.

In order to the make aforementioned and other objects, features and advantages of the present invention comprehensible, preferred embodiments accompanied with figures are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

The embodiments of the present invention are illustrated with reference to the drawings hereinafter.

Figure 1:
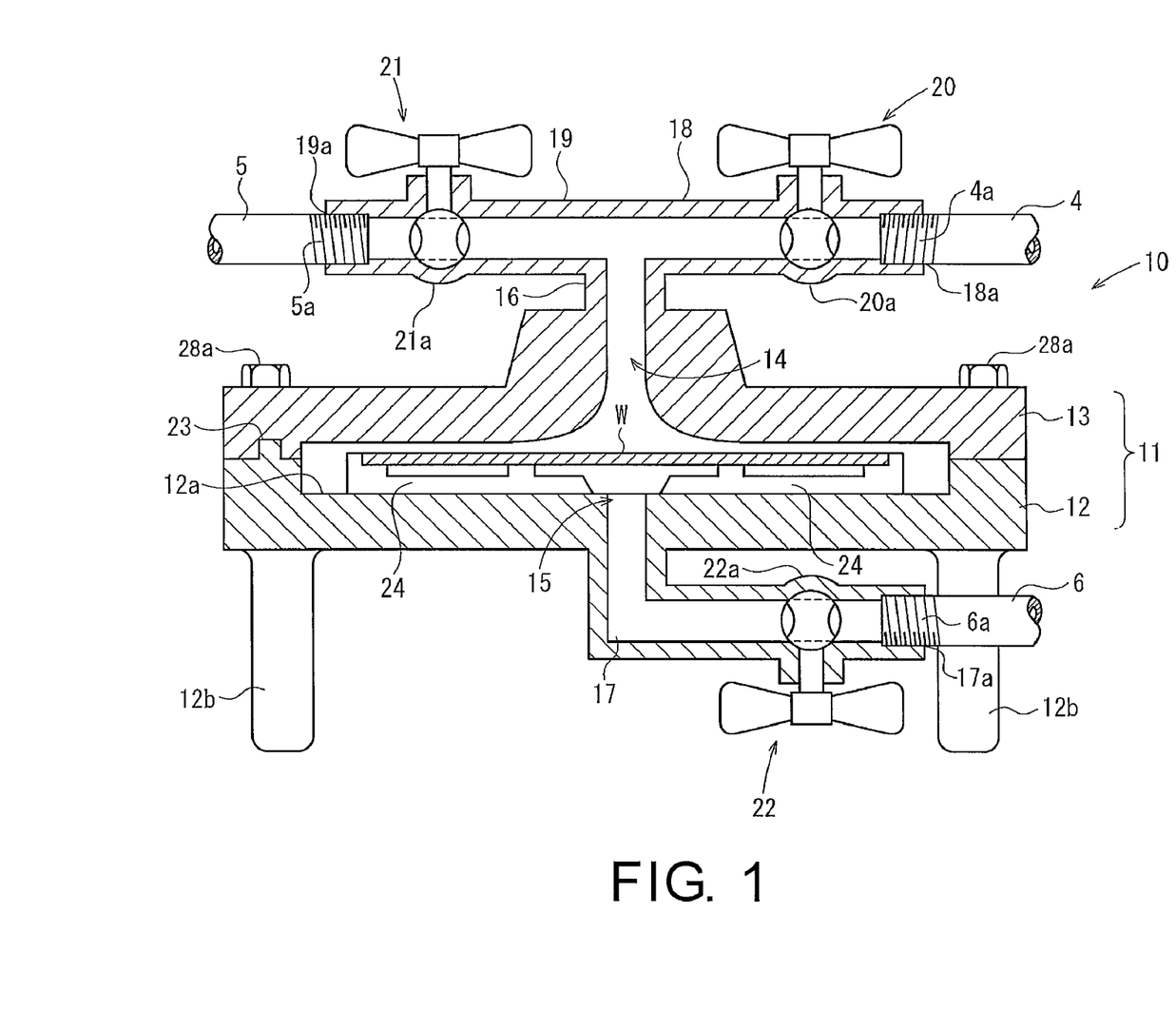
FIG. 1 is a longitudinal sectional view of a substrate contacting apparatus used in a water quality evaluation method according to an embodiment.
Figure 2:
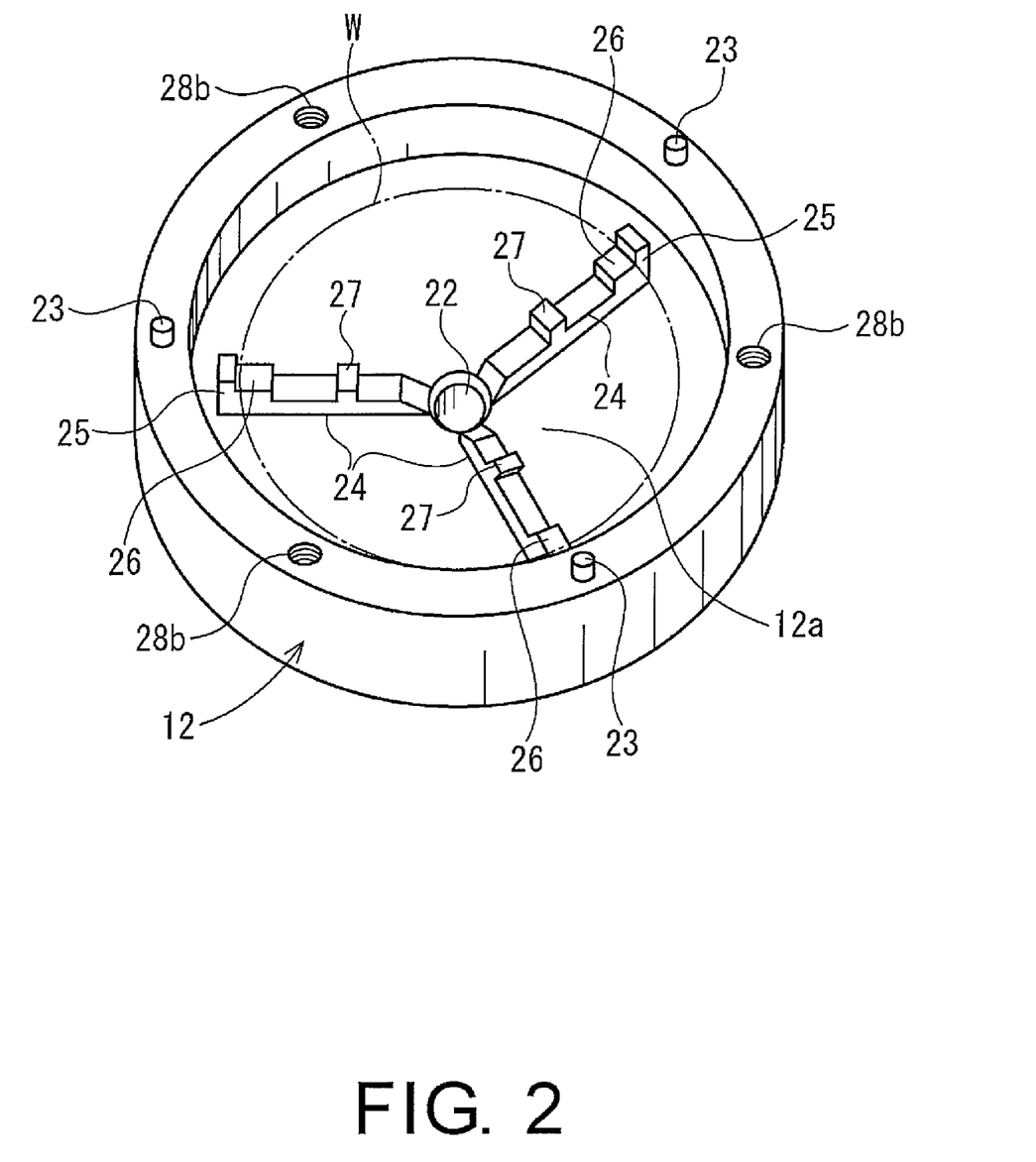
FIG. 2 is a perspective view of a chassis of the substrate contacting apparatus.
Figure 3:
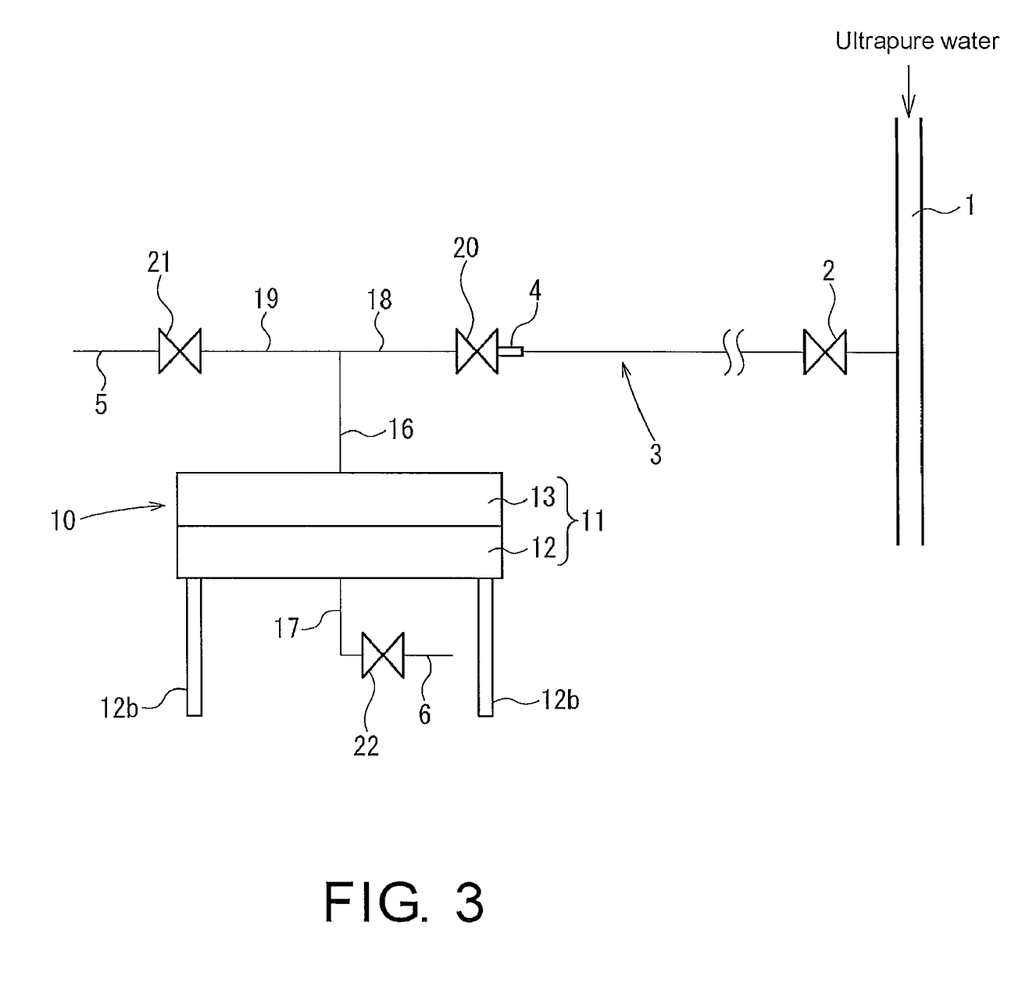
FIG. 3 is a schematic view of a water supply system for supplying water to the substrate contacting apparatus.
Figure 4:
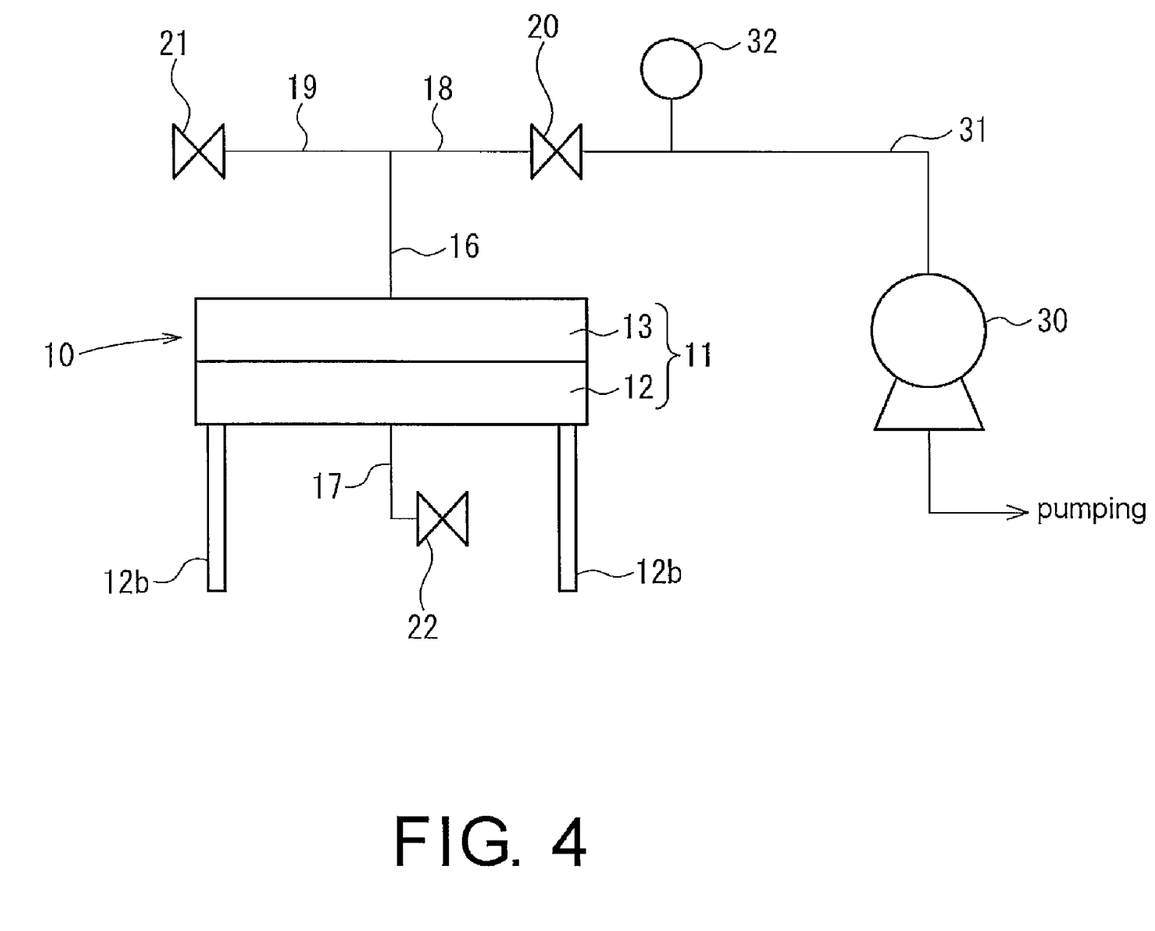
FIG. 4 is a schematic view of an exhaust system for performing sealing performance test on the substrate contacting apparatus.
Figure 5:
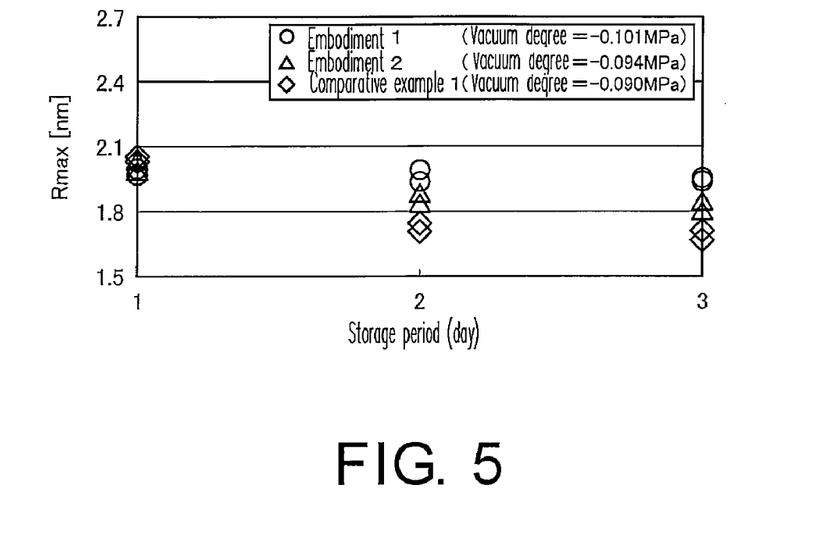
FIG. 5 is a diagram showing test results of the embodiments and a comparative example.
Figure 6:
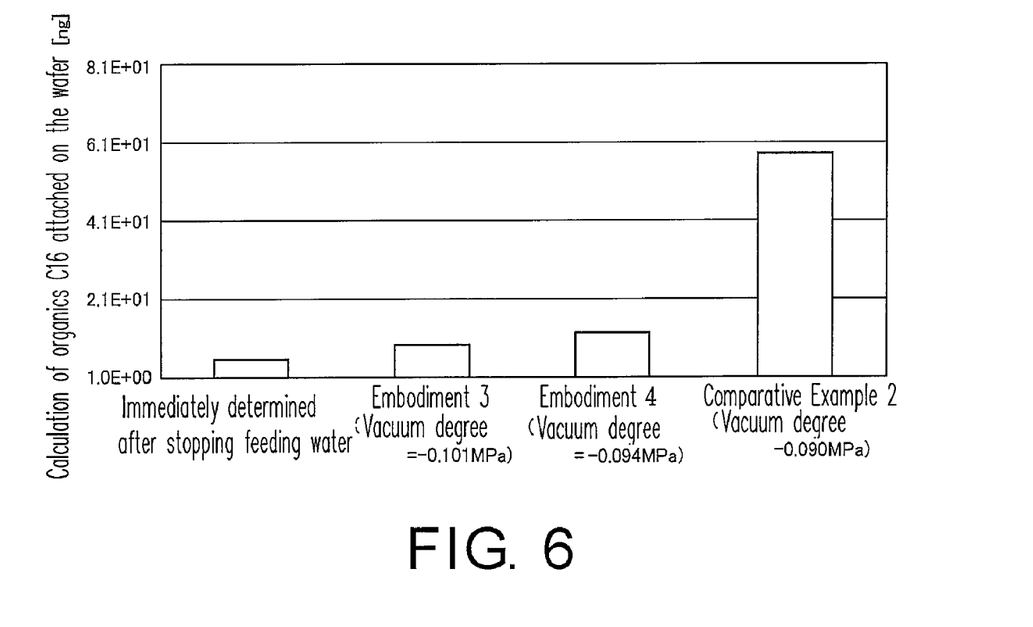
FIG. 6 is a diagram showing test results of the embodiments and a comparative example.
Figure 7:
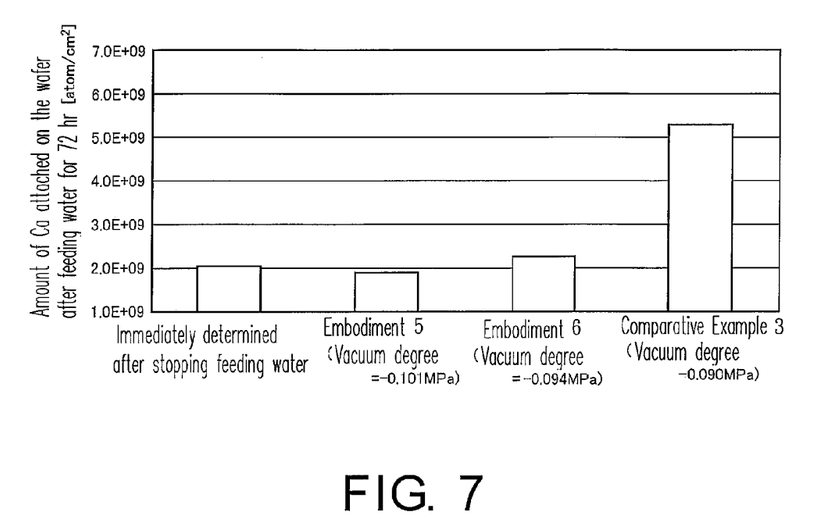
FIG. 7 is a diagram showing test results of the embodiments and a comparative example.
Figure 8:
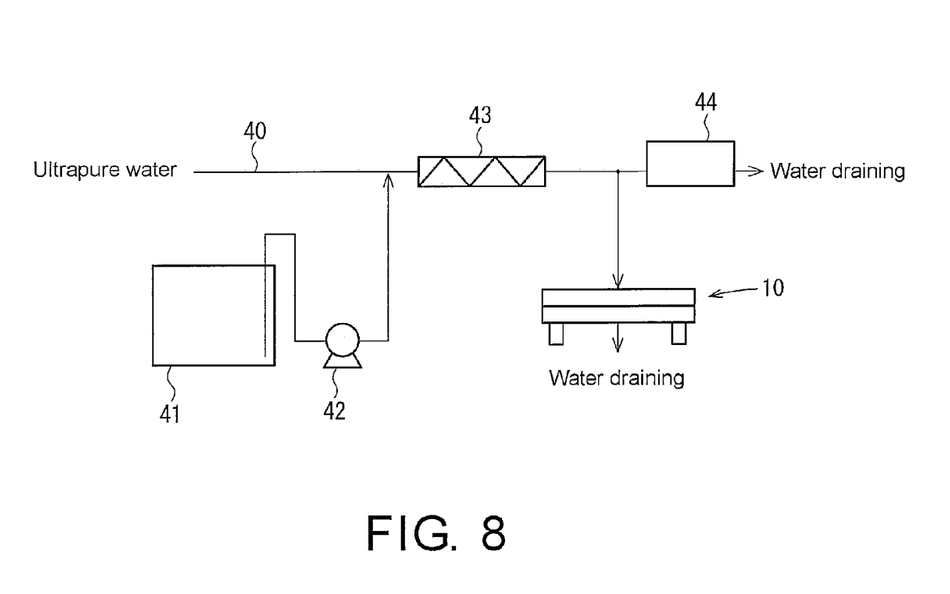
FIG. 8 is a schematic view of a water supply system for performing a test of injecting organics to the substrate contacting apparatus.
Figure 9:
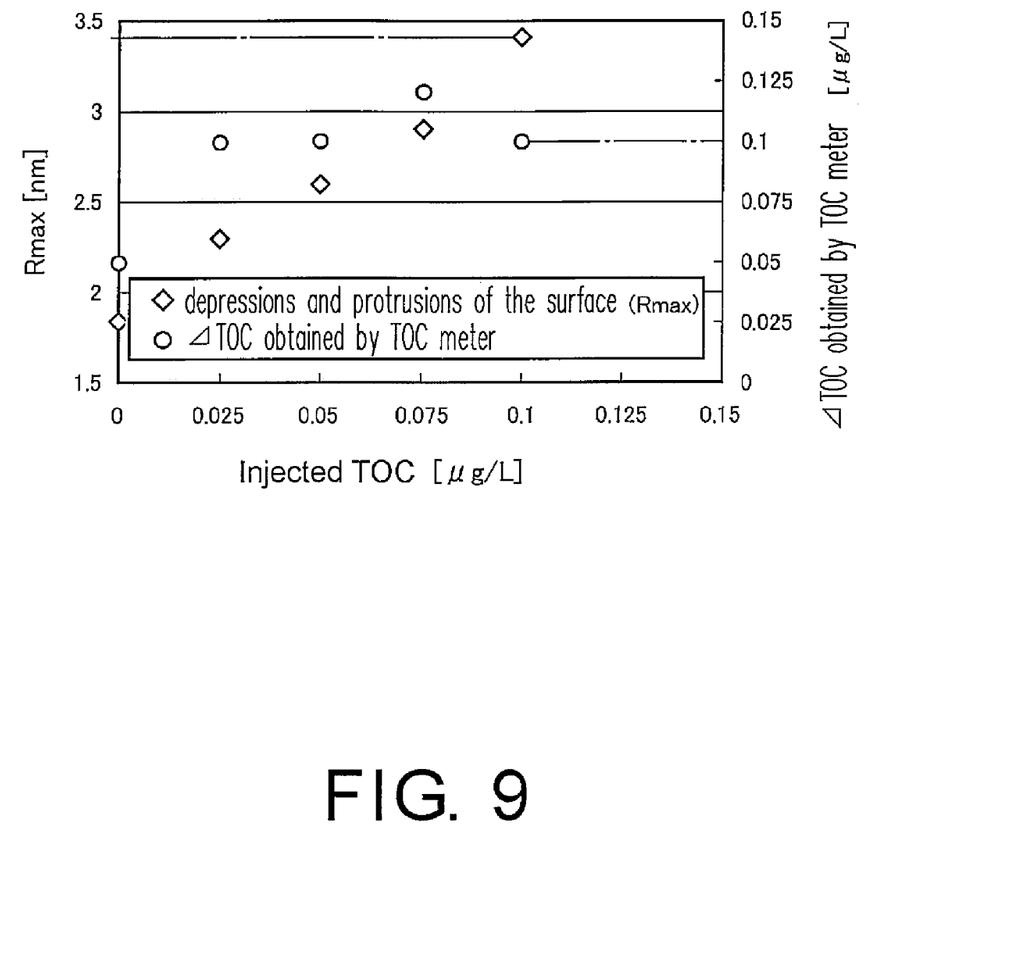
FIG. 9 is a diagram showing the relationship between the determined value of the surface depressions and protrusions of the substrate and the amount of injected total organic carbon (TOC).

FIG. 1 is a longitudinal sectional view of a substrate contacting apparatus used in a water quality evaluation method according to an embodiment. FIG. 2 is a perspective view of a chassis of the substrate contacting apparatus. FIG. 3 is a schematic view of a water supply system for supplying water to the substrate contacting apparatus. FIG. 4 is a schematic view of an exhaust system for performing sealing performance test on the substrate contacting apparatus. FIGS. 5-7 are diagrams showing test results according to embodiments and comparative examples. FIG. 8 is a schematic view of a water supply system for performing a test of injecting organics to the substrate contacting apparatus. FIG. 9 is a diagram showing the relationship between the determined value of the surface depressions and protrusions of the substrate and the amount of injected total organic carbon (TOC).

[Substrate Used in Water Quality Evaluation]

Preferably, the substrate used in the water quality evaluation method of the present invention is a silicon wafer cut from any crystal including n-type silicon, p-type silicon, or monocrystalline silicon with an inclined angle from a surface (001) of the crystal. The inclined angle of the cut silicon wafer is preferably in a range of 3-5° towards a direction (011) with respect to the surface (001). For example, if a 4° Off-type silicon wafer is used, the evaluation can be performed under the circumstance that the whole silicon crystal is exposed, so more strict evaluation can be performed.

[Substrate Contacting Apparatus 10]

The substrate contacting apparatus 10 of this embodiment has a container body 11, which includes a chassis 12 having a circular recess 12*a* for accommodating a substrate W on the upper surface thereof and a cover 13 for sealing the recess 12*a*. A water supply port 14 for supplying the water to be evaluated (ultrapure water) to the recess 12*a* is disposed approximately at the center of the cover 13. A water drain port 15 for draining the water to be evaluated out of the recess 12*a* is disposed approximately at the center of the bottom of the recess 12*a*. Symbol 12*b* indicates feet vertically disposed downward from the lower surface of the chassis 12. Furthermore, when the substrate contacting apparatus 10 is substantially disposed on a horizontal plane, the feet 12*b* support the substrate contacting apparatus 10 to make it substantially horizontal.

A water supply pipe 16 is connected to the water supply port 14, and a water drain pipe 17 is connected to the water drain port 15. Two bypasses, namely an inlet pipe 18 and an outlet pipe 19 are branched at the upstream of the water supply pipe 16. Moreover, in this embodiment, the inlet pipe 18 and the outlet pipe 19 extend in opposite directions with their center lines being substantially at a straight line, and the water supply pipe 16 extends in a direction substantially orthogonal to the inlet pipe 18 and the outlet pipe 19. However, if the inlet pipe 18 and the outlet pipe 19 are branched into two bypasses, the center lines can also be not at a straight line. Furthermore, in this embodiment, the water drain pipe 17 extends downward from the water drain port 15, and is bent to a direction in a substantially right angle at midway, however, it can also extend downward directly.

On-off valves 20, 21, and 22 are respectively disposed at midway of the extension directions of the inlet pipe 18, the outlet pipe 19, and the water drain pipe 17. In this embodiment, the on-off valves 20-22 are composed of ball valves with high tightness upon being sealed.

In this embodiment, the cover 13, the water supply pipe 16, the inlet pipe 18, the outlet pipe 19, and valve chambers 20*a*, 21*a* of the on-off valves 20, 21 are formed into one piece. Additionally, the chassis 12, the water drain pipe 17, and the valve chamber 22*a* of the on-off valve 22 are also formed into one piece. However, if the tightness of the junctions of the means is sufficiently ensured, they can also be formed separately.

A sampling pipe 3 for supplying water to be evaluated to the substrate contacting apparatus 10 branches from an ultrapure water supplying pipe 1 through an on-off valve 2. The sampling pipe 3 is connected to a pipe joint 4 by being external inlayed and fixed with a band or screwed. The sampling pipe 3 and the pipe joint 4 form the supplying pipe of the water to be evaluated.

An internal thread (with the symbol omitted) is formed on the internal surface of a mouthpiece 18*a* at the upstream side of the inlet pipe 18, and an external thread 4*a* screwed with the internal thread is formed at the external surface of the front end of the pipe joint 4. Therefore, the pipe joint 4 is detachably screwed in the mouthpiece 18*a* of the inlet pipe 18. As described above, the inlet pipe 18 and pipe joint 4 are connected by screwing, thereby obtaining preferred tightness of the junction.

A mouthpiece 19*a* at the downstream side of the outlet pipe 19 and a mouthpiece 17*a* at the downstream side of the water drain pipe 17 are respectively connected with draining pipes 5, 6 for guiding water from the outlet pipe 19 and the water drain pipe 17 into drainage system. The pipes 5, 6 are connected with the mouthpieces 19*a*, 17*a* of the outlet pipe 19 and the water drain pipe 17 also by screwing. That is to say, internal threads (with the symbol omitted) are formed on the internal surfaces of the mouthpieces 19*a*, 17*a*, and external threads 5*a*, 6*a* screwed with the internal threads are formed at the external surfaces of the front ends of the pipes 5, 6. The pipes 5, 6 are also detachably screwed to the mouthpieces 19*a*, 17*a*.

However, as the pipes 5, 6 are on the water draining side, it is unnecessary to consider the tightness of the connection of the pipes 5, 6 and the mouthpieces 19*a*,17*a*. Accordingly, the connection of the pipes 5, 6 and the valves 21, 22 can also be realized by means other than screwing. The connection of the pipe joint 4 and valve 20 is not required to be realized by screwing, but the pipe joint 4 and the valve 20 are on the water supplying side, so they are preferably be screwed with high tightness.

The circular recess 12*a* of the chassis 12 has an inner diameter sufficiently larger than the diameter of the substrate W to be hold therein. On the bottom of the recess 12*a*, a plurality of (in this embodiment, 3) radial ridges 24 rising at same intervals are disposed in a circumferential direction to serve as a mechanism for holding the substrate W. Each radial ridge 24 extends in the radius direction of the recess 12*a*.

The substrate W is substantially horizontally held on the radial ridges 24 with the plated surface facing upwards. A stepped support 25 is disposed on external portion of each ridge 24, and has a step 26 for supporting the edge of the substrate W. The height of the step 26 is corresponding to the thickness of the substrate W. Additionally, a support portion 27 projects at midway in the extension direction of each ridge 24 and supports the lower surface in the radius direction of the substrate W at midway.

A plurality of projecting portions 23 for determining the position of the cover 13 projects from the upper surface of the chassis 12. The projecting portions 23 are disposed in the circumferential direction of the recess 12a at substantially same interval. Concave portions (not shown) engaged with the projecting portions 23 are disposed on the lower surface of the cover 13. Symbol 28b indicates a bolt hole in which a bolt 28a is screwed to fix the cover 13 on the chassis 12.

[Sealing Performance Evaluation and Test of the Substrate Contacting Apparatus 10]

Next, the sequence of the sealing performance evaluation and test of the substrate contacting apparatus 10 of the structure is illustrated.

As shown in FIG. 4, a suction pipe 31 connected with a vacuum pump 30 is connected to the mouthpiece 18a of the inlet pipe 18. According to the present invention, a vacuum pump having an ultimate vacuum degree of −0.1012 MPa, and a pumping speed of 20 NL/min is used as the vacuum pump 30. A pressure gauge 32 is disposed in the middle of the suction pipe 31 to detect the pressure in the substrate contacting apparatus 10.

After the cover 13 is covered on the chassis 12 and is fixed (sealed), the on-off valves 21, 22 of the outlet pipe 19 and the water drain pipe 17 are closed, and the on-off valve 20 of the inlet pipe 18 is opened, under this condition, the vacuum pump 30 works to vacuum the interior of the substrate contacting apparatus 10. Furthermore, when the pressure drop of the interior of the substrate contacting apparatus 10 substantially stops, the difference between the measured value of the pressure gauge 32 and the atmospheric pressure is calculated, so as to get the ultimate vacuum degree in the substrate contacting apparatus 10.

In the substrate contacting apparatus 10 of the present invention, the ultimate vacuum degree is preferably lower than or equal to −0.094 MPa, and more preferably lower than or equal to −0.101 MPa.

[Water Quality Evaluation Sequence of Ultrapure Water]

Next, the sequence of the water quality evaluation of the ultrapure water by using the substrate contacting apparatus 10 is illustrated.

Firstly, the substrate W is disposed in the recess 12a, the cover 13 is covered on the chassis 12 and fixed thereon by the bolts 28a. Next, as shown in FIG. 3, the sampling pipe 3 for supplying the water to be evaluated is connected to the mouthpiece 18a of the inlet pipe 18 through the pipe joint 4. Further, the draining pipes 5, 6 are connected to the mouthpieces 19a 17a of the outlet pipe 19 and the water drain pipe 17.

Next, the on-off valve 2 of the sampling pipe 3 and the on-off valves 20, 21 of the inlet pipe 18 and the outlet pipe 19 are opened, such that the water to be evaluated flows through the inlet pipe 18 and the outlet pipe 19, so as to clean the pipes.

Then, the on-off valve 22 of the water drain pipe 17 is opened to feed the water to be evaluated into the substrate contacting apparatus 10 (in the recess 12a), so as to contact the water to be evaluated and the substrate W.

At this time, the opening degree of the on-off valve 20 on the inlet pipe 18 side is fixed, under this condition, the opening degree of the on-off valve 21 on the outlet pipe 19 side is adjusted to adjust the flow rate of the water to be evaluated. Furthermore, it is considerable to adjust the flow rate of the water to be evaluated by adjusting the opening degree of the on-off valve 20 on the inlet pipe 18 side. If it is operated in this manner, the material of the valve structures may be dissolved in the water to be evaluated due to the friction between the parts upon operating, or particles may be blended into the water to be evaluated. Accordingly, when adjusting the opening degree of the on-off valve 21 on the outlet pipe 19 side to adjust the flow rate of the water to be evaluated, even the structure material of the on-off valve 21 is dissolved into the water to be evaluated or particles is blended into the water to be evaluated, as the on-off valve 21 is located at the downstream side of the water supply pipe 16, water supplied to the substrate contacting apparatus 10 will not be contaminated.

After feeding the water to be evaluated into the substrate contacting apparatus 10 for a predetermined time, valves 2, 20-22 are closed to stop feeding water and seal the water in the substrate contacting apparatus 10. Then, the pipe joint 4 is taken off from the mouthpiece 18a.

Afterwards, the substrate contacting apparatus 10 is transported to a substrate analysis device in a sate that the substrate W is accommodated in the substrate contacting apparatus 10. Then, after arriving at the substrate analysis device, the substrate W is taken out from the substrate contacting apparatus 10 in a clean room to analyze the surface state of the substrate W.

[Method for Determining Surface State of the Substrate W]

Method for determining the surface state of the substrate W includes determination of the depressions and protrusions on the surface of the substrate W caused by contacting with the water to be evaluated, determination of attachments attached on the surface of the substrate W, or determination of oxide film generated on the surface of the substrate W.

(1) Determination of depressions and protrusions of the surface of the substrate W.

The depressions and protrusions of the substrate surface can be determined by using a scanning probe microscope, such as an atomic force microscope (AFM), a scanning tunneling microscope (STM) and a magnetic force microscope (MFM), and preferably AFM.

It is known that there are three determination modes of AFM, namely, non-contact mode, contact mode, and tapping mode. Any of the modes can be used, and the tapping mode will not damage the substrate and has high determination capability, so it is preferred.

The determination indexes of the depressions and protrusions of the substrate surface are listed as follows:

(a) height difference (Rmax, in nm) between the highest portion and the lowest portion in the depressions and protrusions of the substrate surface.

(b) average value (Ra, in nm) of the height difference of the depressions and protrusions of the substrate surface.

(c) root mean square roughness (Rms) of the depressions and protrusions of the substrate surface.

Here, the evaluation can be performed by using one of the indexes or combination of two or more indexes.

(2) Determination of attachments attached on the surface of the substrate W or oxide film generated on the surface of the substrate W.

During the determination of the attachments on the surface of the substrate W, the substances have unfavorable influence on the substrate W are the objects, and the representative substances are, for example, metals (such as Na, K, Ca, Al, Fe, Cu, and Ni) and organics (such as various amines and polystyrenesulfonic acid).

The attachments attached on the surface of the substrate W can be determined by fluorescence X-ray analysis, gas chromatograph-mass spectrometry, or Auger electron spectroscopy analysis. The fluorescence X-ray analysis is suitable for determining metals attached on the surface of the substrate W, the gas chromatograph-mass spectrometry is suitable for determining organics, and the Auger electron spectroscopy analysis is suitable for determining metals and organics. Furthermore, the Auger electron spectroscopy analysis can also be used to determine the oxide film generated on the surface of the substrate W.

When determining the attachments attached on the surface of the substrate W, the attachments on the substrate W can be determined directly, alternatively, the attachments can be temporarily eluted and then retrieved, and then the eluant is analyzed.

However, other determining methods in addition to the above methods can also be used to analyze the surface state of the substrate W.

[Effects of the Water Quality Evaluation Method Using the Substrate Contacting Apparatus 10]

In the method for evaluating quality of the water to be evaluated using the substrate contacting apparatus 10 according to the present invention, the substrate contacting apparatus 10 has high sealing performance that can keep the interior at a vacuum degree lower than or equal to −0.094 MPa. Therefore, the invasion of the air into the substrate contacting apparatus 10 to contact the substrate can be prevented or significantly inhibited after feeding the water to be evaluated into the substrate contacting apparatus 10 with the substrate W accommodated therein to contact the water to be evaluated and the substrate W. Therefore, the substrate W is completely or almost not influenced by the air. As a result, the evaluation of the quality of the water to be evaluated can be performed with high precision (determining amounts of metals or organics in water to be evaluated).

Furthermore, in the present invention, the surface state of the substrate W contacting the water to be evaluated is determined, such that the influences of the water to be evaluated on the substrate W (formation of the depressions and protrusions, attachment of the contamination, or generation of the oxide film on the surface of the substrate W) can be actually known.

That is to say, for example, certain substances exist in the water to be evaluated in an extreme micro amount, and have unfavorable influence on the substrate W due to the influence of co-existing substances, such a situation cannot be known by directly analyzing the quality of the water to be evaluated, however, it can be known by actually analyzing the surface state of the substrate W.

Furthermore, for example, during analyzing the quality of the water to be evaluated, even the substance forming the depressions and protrusions cannot be determined due to the concentration thereof being lower than or equal to the lower limit value, or even the substance is an unknown substance, if it is possible to determine the depressions and protrusions of the substrate W, it is possible to evaluate the quality of the water to be evaluated.

EMBODIMENTS

Hereinafter, the present invention is further illustrated in detail with reference to the embodiments and the comparative examples.

Embodiments 1, 2 and Comparative Example 1

Embodiment 1

As a substrate, a Si wafer was accommodated in a substrate contacting apparatus at an ultimate vacuum degree of −0.094 MPa. According to the sequence of the embodiment, ultrapure water was fed into the substrate contacting apparatus to contact the Si wafer, and each valve was closed to stop feeding water, so as to make the interior of the substrate contacting apparatus in a sealed state. Afterwards, the substrate contacting apparatus was stored with the Si wafer accommodated therein. The temperature of the external gas was 25° C. during the storage.

The height difference (Rmax) between the highest portion and the lowest portion in the depressions and protrusions of the Si wafer surface was determined on the first day, the second day, and the third after stopping feeding water. The results are shown in FIG. 5.

Embodiment 2

This is a repetition of Embodiment 1 except that, a Si wafer was accommodated in a substrate contacting apparatus at an ultimate vacuum degree of −0.101 MPa and ultrapure water was fed into the substrate contacting apparatus. The Rmax of the Si wafer surface was determined on the first day, the second day, and the third after stopping feeding water. The results are shown in FIG. 5.

Comparative Example 1

This is a repetition of Embodiment 1 except that, a Si wafer was accommodated in a substrate contacting apparatus at an ultimate vacuum degree of −0.090 MPa and ultrapure water was fed into the substrate contacting apparatus. The Rmax of the Si wafer surface was determined on the first day, the second day, and the third after stopping feeding water. The results are shown in FIG. 5.

Embodiments 3, 4 and Comparative Example 2

Embodiment 3

Similar to Embodiment 1, a Si wafer was accommodated in a substrate contacting apparatus at an ultimate vacuum degree of −0.094 MPa, ultrapure water was fed into the substrate contacting apparatus, and the interior of the substrate contacting apparatus was kept at a sealed state. Afterwards, the substrate contacting apparatus was stored with the Si wafer accommodated therein. The temperature of the external gas was 25° C. during the storage.

On the third day after stopping feeding water, the amounts of organics attached on the surface of the Si wafer were determined by means of thermal desorption-gas chromatograph/mass spectrometry (TD-GC/MS). The results are shown in FIG. 6. Additionally, the results of the amounts of the organics attached on the surface of the Si wafer immediately determined after stopping feeding water are together shown in FIG. 6.

Embodiment 4

This is a repetition of Embodiment 3 except that, a Si wafer was accommodated in a substrate contacting apparatus at an ultimate vacuum degree of −0.101 MPa and ultrapure water was fed into the substrate contacting apparatus. The amounts of organics attached on the surface of the Si wafer were determined on the third day after stopping feeding water. The results are shown in FIG. 6.

Comparative Example 2

This is a repetition of Embodiment 3 except that, a Si wafer was accommodated in a substrate contacting apparatus at an ultimate vacuum degree of −0.090 MPa and ultrapure water was fed into the substrate contacting apparatus. The amounts of organics attached on the surface of the Si wafer were measured on the third day after stopping feeding water. The results are shown in FIG. 6.

Embodiments 5, 6 and Comparative Example 3

Embodiment 5

Similar to Embodiment 1, a Si wafer was accommodated in a substrate contacting apparatus at an ultimate vacuum degree of −0.094 MPa, ultrapure water was fed into the substrate contacting apparatus, and the interior of the substrate contacting apparatus was kept at a sealed state. Afterwards, the substrate contacting apparatus was stored with the Si wafer accommodated therein. The temperature of the external gas was 25° C. during the storage.

On the third day after stopping feeding water, the amount of Ca attached on the surface of the Si wafer were determined by means of total reflection fluorescence X-ray analysis. The results are shown in FIG. 7. Additionally, the results of the amount of Ca attached on the surface of the Si wafer immediately determined after stopping feeding water are together shown in FIG. 7.

Embodiment 6

This is a repetition of Embodiment 5 except that, a Si wafer was accommodated in a substrate contacting apparatus at an ultimate vacuum degree of −0.101 MPa and ultrapure water was fed into the substrate contacting apparatus. The amount of Ca attached on the surface of the Si wafer was determined on the third day after stopping feeding water. The results are shown in FIG. 7.

Comparative Example 3

This is a repetition of Embodiment 5 except that, a Si wafer was accommodated in a substrate contacting apparatus at an ultimate vacuum degree of −0.090 MPa and ultrapure water was fed into the substrate contacting apparatus. The amount of Ca attached on the surface of the Si wafer was determined on the third day after stopping feeding water. The results are shown in FIG. 7.

FIGS. 5 to 7 show that, if the substrate contacting apparatus has a high tightness at an ultimate vacuum degree lower than or equal to −0.094 MPa, after stopping feeding the ultrapure water, the surface state of the Si wafer (the size of the depressions and protrusions and the amounts of the attached organics and metals) is not changed with time or changed a little, so the substrate can be kept in the substrate contacting apparatus for a long time.

[Relationship Between the Determined Values of the Depressions and Protrusions of the Substrate Surface and the Amounts of the Organics in the Water to be Evaluated]

The relationship between the determined values of the depressions and protrusions of the substrate surface contacting the water to be evaluated and the amounts of the organics in the water to be evaluated is investigated by using a water supply system in FIG. 8.

In the water supply system in FIG. 8, organics (amine compounds) is injected through a pump 42 from an organic tank 41 at the upstream side of a water supply pipeline 40 of the ultrapure water (water to be evaluated). A pipeline mixer 43 is disposed in the middle of the water supply pipeline 40 (at downstream side of the organic injection point). At the downstream side of the pipeline mixer, the water supply pipeline 40 branches into two bypasses, one bypass is connected to the substrate contacting apparatus 10, and the other is connected to a TOC meter.

The output of the pump 42 is adjusted by using the water supply system, such that the theoretical TOC amount injected into the ultrapure water is 0.1 μg/L, 0.075 μg/L, 0.05 μg/L, and 0.025 μg/L, and the ultrapure water is fed into the substrate contacting apparatus 10. The results of the depressions and protrusions (Rmax) of the substrate surface determined after feeding the ultrapure water with various amounts of TOC injected are shown in FIG. 9. Further, the measured values of the TOC meter upon feeding the water with various amounts of TOC injected are also shown in FIG. 9.

As shown in FIG. 9, although the injected TOC amount is increased, the measured valued of TOC meter 44 is not increased accordingly, so the measurement precision is not high. However, the determined values of the depressions and protrusions (Rmax) of the substrate surface are increased also in proportional to the increment of the injected TOC amount, which accurately reflects the injected TOC amount. Therefore, it is known that the influence of the water to be evaluated on the substrate can be known by determining the depressions and protrusions of the substrate surface.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A water quality evaluation method, comprising:
   providing a substrate contacting apparatus;
   performing a sealing performance evaluation of the substrate contacting apparatus by connecting the substrate contacting apparatus to a vacuum pump, creating a pressure drop in the substrate contacting apparatus with the vacuum pump, measuring an interior pressure of the substrate contacting apparatus when the pressure drop in the substrate contacting apparatus substantially stops, and calculating a difference between the interior pressure of the substrate contacting apparatus and atmospheric pressure;
   accommodating the substrate in the substrate contacting apparatus when the calculated pressure difference is lower than or equal to −0.094 MPa;
   feeding water to be evaluated into the substrate contacting apparatus to contact the substrate;
   sealing the substrate in the substrate contacting apparatus;
   transporting the substrate contacting apparatus with the substrate accommodated therein to an analysis device;
   taking the substrate out of the substrate contacting apparatus; and
   determining a substrate surface state to evaluate water quality.

2. The water quality evaluation method as claimed in claim 1, wherein the determining of the substrate surface state is determining the depressions and protrusions of the substrate surface.

3. The water quality evaluation method as claimed in claim 2, wherein the depressions and protrusions of the substrate surface is determined by a scanning probe microscope.

4. The water quality evaluation method as claimed in claim 3, wherein the scanning probe microscope is an atomic force microscope (AFM).

5. The water quality evaluation method as claimed in claim 1, wherein the determining of the substrate surface state is determining substances attached or formed on the substrate surface.

6. The water quality evaluation method as claimed in claim 5, wherein the substances attached or formed on the substrate surface are determined by fluorescence X-ray analysis, gas chromatograph-mass spectrometry, or auger electron spectroscopy analysis.

* * * * *